United States Patent [19]

Iimuro et al.

[11] Patent Number: 4,918,245
[45] Date of Patent: Apr. 17, 1990

[54] PROCESS FOR PREPARING BISPHENOL A

[75] Inventors: Shigeru Iimuro; Takashi Kitamura, both of Nagoya; Yoshio Morimoto, Tokai, all of Japan

[73] Assignee: Mitsui Toatsu Chemicals, Inc., Tokyo, Japan

[21] Appl. No.: 276,658

[22] Filed: Nov. 28, 1988

[30] Foreign Application Priority Data

Dec. 4, 1987 [JP] Japan ................................ 62-305942

[51] Int. Cl.$^4$ ...................... C07C 37/20; C07C 39/16
[52] U.S. Cl. .................................... 568/727; 568/722; 568/723; 568/738
[58] Field of Search ............... 568/727, 728, 724, 722, 568/721, 723, 725, 726, 730

[56] References Cited

U.S. PATENT DOCUMENTS

| 2,359,242 | 9/1944 | Perkins et al. | 568/727 |
| 3,172,916 | 3/1965 | Wagner | 568/728 |
| 3,221,061 | 11/1965 | Grover et al. | 568/728 |
| 4,188,496 | 2/1980 | Jaquiss et al. | 568/728 |
| 4,308,404 | 12/1981 | Kwantes et al. | 568/727 |
| 4,584,416 | 4/1986 | Pressman et al. | 568/727 |

FOREIGN PATENT DOCUMENTS 1342760 10/1963 France ........................ 568/427

Primary Examiner—Werren B. Lone
Attorney, Agent, or Firm—Burns, Doane, Swecker & Mathis

[57] ABSTRACT

This invention is a process for the preparation of bisphenol A from acetone and phenol. By this invention, the formation of by-products is extremely decreased and post treatment steps can be simplified.

This invention involves the following steps. (1) One mole of acetone is reacted with 4 to 12 moles of phenol in the presence of a sulfonic acid type cation exchange resin catalyst modified with a mercapto group-containing compound such as mercaptoethylamine to convert 20 to 60% of acetone, and (2) the reaction mixture containing unreacted acetone is successively reacted in the presence of the hydrochloric acid catalyst.

The formation of by-products such as 2-(2-hydroxyphenyl)-2-(4-hydroxyphenyl)propane, Dianin's compound and the like is remarkably reduced by the process of this invention.

7 Claims, 1 Drawing Sheet

4,918,245

PROCESS FOR PREPARING BISPHENOL A

BACKGROUND OF THE INVENTION

The present invention relates to a process for preparing bisphenol A of high purity, that is, 2,2-bis(4-hydroxyphenyl)propane of high purity.

Bisphenol A is used as a raw material for polycarbonate resins or epoxy resins. Colorless and highly purified bisphenol A is particularly required for polycarbonate resins.

Bisphenol A is prepared by the reaction of acetone with excess phenol in the presence of an acid catalyst or a combination of an acid catalyst and a cocatalyst such as sulfur compounds.

The reaction mixture contains, in addition to bisphenol A, catalyst, unreacted acetone, unreacted phenol, water and other by-products formed by the reaction.

Principal components of the by-products are 2-(2-hydroxyphenyl)-2-(4-hydroxyphenyl)propane (hereinafter referred to as o,p'-isomer) and 2,2,4-trimethyl-4-(4-hydroxyphenyl)chroman (hereinafter referred to as Dianin's compound). Other components such as trisphenol, polyphenol and unfavorable colored substances are also included. These by-products deteriorate the properties of the resin prepared from bisphenol A.

As the catalyst of the condensation reaction, hydrochloric acid and strongly acidic ion exchange resins have been known to date.

When hydrochloric acid is used as the catalyst, the reaction can proceed at lower temperatures with successive crystallization of adduct of bisphenol A and phenol. In the course of the reaction, the o,p'-isomer in the mother liquor is converted to bisphenol A and hence the amount of the o,p'-isomer is decreased. The reaction with hydrochloric acid catalyst, however, generates a large amount of Dianin's compound as a by-product. As a method for lowering the generation of Dianin's compound, the addition of water has been disclosed by Progil in Japanese Patent Publication, TOKKOSHO 40-7186 (1965). The addition of mercapto compounds has also been reported by Dow Chemical Co. in Japanese Patent Publication, TOKKOSHO 27-5367 (1952). These methods, however, are unfavorable because of complex procedures for the separation and recovery of hydrochloric acid and mercapto compounds as well as the obnoxious odor resulting from mercapto compounds. The generation of Dianin's compound can be reduced by using a greater excess of phenol. On the other hand, the formation of o,p'-isomer increases and a large excess of phenol used must be recovered.

When commonly used ion exchange resins of the strong acid type are employed, by-products are produced in a large amount. Particularly when an ion exchange resin is used for the catalyst, the isomerization due to crystallization of the adduct of bisphenol A and phenol cannot be utilized and thus o,p'-isomer is formed in a much larger amount when compared to the use of hydrochloric acid catalyst.

When the functional groups of the ion exchange resin are modified with mercapto groups such as by reaction with a mercaptoalkylamine, it has been known to markedly decrease the amount of Dianin's compound produced. o,p'-Isomer, however, is still formed as a by-product in a large amount because crystallization of the adduct cannot be utilized.

When an ion exchange resin is used, water formed in the reaction leads to insufficient conversion of acetone. As a result, dehydration of the ion exchange resin is needed in every batchwise reaction. An enormous amount of the resin is also required in a continuous reaction in order to proceed with the conversion of acetone to a significant extent. These results are disclosed by Mitsui Toatsu Chemicals, Inc. in Japanese Laid-Open Patent Publication, TOKKAISHO 61-78741 (1986).

As mentioned above, previously known processes for preparing bisphenol A could not satisfactorily inhibit the formation of two typical impurities, although these processes have their own characteristics, respectively.

SUMMARY OF THE INVENTION

The object of this invention is to provide a process for preparing bisphenol A of high purity with a minimum amount of by-products and impurities formed in the reaction as well as the simplest procedure in post treatment steps.

DETAILED DESCRIPTION OF THE INVENTION

Figure 1:
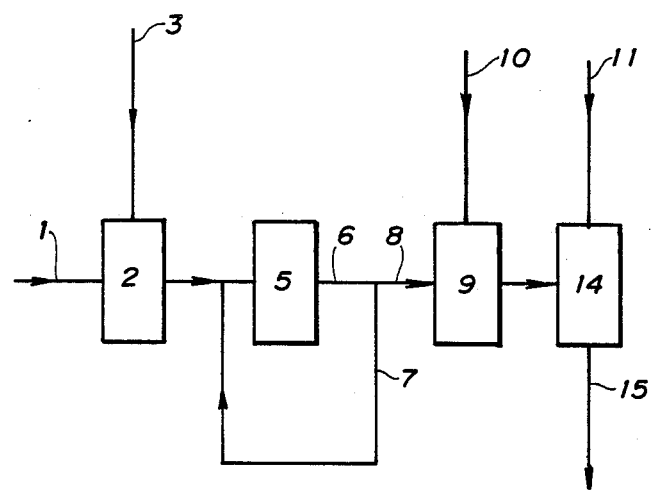
FIG. 1 is a flow diagram illustrating an embodiment of this invention for the preparation of bisphenol A.

The present inventors have carried out an intensive investigation in order to achieve the above mentioned objects. As a result, it has been found that the objects of this invention can be achieved by reacting a part of the acetone with excess phenol in the presence of a specific ion exchange resin and then further reacting the resultant reaction mixture in the presence of a hydrochloric acid catalyst. Thus the present invention has been achieved.

That is, the present invention is a process for preparing bisphenol A by the reaction of acetone with phenol comprising:

(a) conducting the reaction of acetone with phenol in the presence of a sulfonic acid type cation exchange resin modified with a mercapto group-containing compound to convert 20 to 60% of the acetone in the reaction; and (b) further reacting the resulting reaction mixture containing unreacted acetone in the presence of a hydrochloric acid catalyst.

In the process of this invention, 1 mole of acetone is usually reacted with 4 to 12 moles of phenol substantially in the absence of a solvent as a third component. The total amount of acetone may be charged to the first reactor containing the cation exchange resin or a part of the acetone may be fed to the second reactor containing the hydrochloric acid catalyst. Each reaction step may be composed of one or several reactors connected with each other in series or in parallel. The reactors may be batchwise or continuous, respectively. A preferred embodiment is to continuously carry out the reaction using the cation exchange resin catalyst and to feed the reaction mixture successively to a plurality of batch reactors containing the hydrochloric acid catalyst. The present invention can be most effectively conducted by applying such a reaction system.

The first reaction is carried out in the presence of the cation exchange resin catalyst.

The reaction is usually conducted under atmospheric pressure at a pressure of 5 kg/cm² and a temperature of 30° to 120° C., preferably 50° to 100° C. When the reaction temperature is lower than 30° C., the reaction rate is too slow. A reaction temperature exceeding 120° C. causes an unfavorable increase of by-product formation. The reactors are heated or cooled, if necessary.

The reaction time usually depends upon the type of reaction and particularly the reaction temperature. For example, in a batch reaction using a stirred reactor, the reaction time is usually 0.1 to 10 hours. In a piston-flow type continuous reaction using a fixed bed catalyst, the reaction is controlled so as to obtain a space velocity of 0.1 to 10/hr. Acetone conversion ratio of 20 to 60% can be achieved by employing the reaction conditions mentioned above.

The resin used in the process of this invention is a sulfonic acid type cation exchange resin modified with a mercapto group-containing compound.

As to the sulfonic acid type cation exchange resin, commercial products usually available in the market can be used. Modification with mercapto group containing compounds are well known to those skilled in the art. The compounds used for the modification include, for example, mercaptoalkylamines, thiazalidine compounds and pyridinealkanethiols. These compounds are disclosed by Dow Chemical Co. in Japanese Patent Publication TOKKOSHO 46-19953 (1971) and Japanese Laid-Open Patent Publication TOKKAISHO 48-71389 (1973) as well as by Mitsubishi Kasei Ltd. in Japanese Laid-Open Patent Publication TOKKAISHO 57-35533 (1982).

The modification method of the resin has been known. The modification can be readily carried out by neutralizing a part of the sulfonic acid groups with mercapto groups as disclosed by Dow Chemical Co. in Japanese Patent Publication 46-19953 (1971) and by Shell International Research Ltd. in Japanese Laid-Open Patent Publication TOKKASHO 53-14680 (1978).

The modification ratio is usually 5 to 35 mole %, preferably 10 to 20 mole % of the sulfonic acid groups in the resin. A modification ratio lower than 5 mole % causes a decrease in the reaction velocity and an increase in the Dianin's compound. A modification ratio exceeding 35 mole % also leads to a decrease in the reaction velocity and conversion rate.

The reaction using the resin catalyst is terminated at an acetone conversion of 20 to 60%. When a conversion rate of more than 60% is obtained, the conversion velocity decreases rapidly due to the generation of water and a huge amount of the catalyst is required as disclosed by Mitsui Toatsu Chemicals, Inc. in Japanese Laid-Open Patent TOKKAISHO 61-78741 (1986). When the reaction proceeds along with continuous removal of generated water, a high conversion ratio can be obtained by a small amount of the resin, but the amount of o,p'-isomer cannot be lowered to less than that obtained by the reaction in the presence of resin.

The second reaction is carried out in the presence of a hydrochloric acid catalyst. The hydrochloric acid catalyst may be supplied in the form of aqueous hydrochloric acid, hydrogen chloride or a mixture thereof. The reaction can be conducted a known manner except that the reaction mixture produced in the presence of the cation exchange resin catalyst is used. The reaction is carried out under agitation at 30° to 85° C., preferably at 35° to 60° C. Hydrogen chloride may be saturated prior to the reaction or continuously fed to the reactor. In consideration of the exothermic absorption of hydrogen chloride, the heat of reaction and the crystallization heat of the adduct, it is preferred to feed hydrogen chloride both prior to and in the course of the reaction. Generated heat is removed by external cooling to control the reaction temperature within the range mentioned above.

Adduct crystals of bisphenol A and phenol are precipitated with the progress of the reaction. The o,p'-isomer in the solution is isomerized to bisphenol A accompanied by the crystallization of the adduct. Thus the concentration of the o,p'-isomer is decreased. The Dianin's compound generates only a slight amount because the acetone charged into the second reaction is in a low concentration.

Water, catalyst and excess phenol are removed from the reaction mixture thus obtained to give bisphenol A.

The resultant bisphenol A is used as the product as it is or can be subjected to further steps for purification and forming to give the product. Colorless bisphenol A of high purity can also be obtained by removing phenol from the crystallized adduct of bisphenol A and phenol.

An example of a flow diagram for carrying out the process of this invention will be briefly described by way of FIG. 1.

Phenol (1) and acetone (3) are mixed in a mixing tank (2) and fed to the reactor (5) containing the cation exchange resin catalyst. Reaction product mixture (6) from the reactor (5) contains unreacted acetone. A part (7) of the reaction product mixture (6) is mixed with the raw materials and recycled again to the first reactor (5). The remainder (8) of the mixture (6) is transferred to a hydrogen chloride absorption column (9) and saturated with hydrogen chloride (10). The resultant mixture is then reacted in the second reactor (14) which is a hydrochloric acid catalyst reactor. The reaction is conducted for several hours to react almost all of the acetone. Thereafter the reaction product (15) is transferred to the purification step. When the amount of hydrochloric acid is insufficient in the course of the reaction in the reactor (14) mentioned above, hydrogen chloride or concentrated hydrochloric acid (11) is supplied to the reactor (14).

EXAMPLE

The process of this invention will hereinafter be described in detail by way of example and comparative examples.

EXAMPLE 1

A sulfonic acid type cation exchange resin was used as the catalyst after modifying 12% of its sulfonic acid groups with mercaptoethylamine. The catalyst was used in the form of a packed layer having a diameter of 30 cm and a length of 200 cm.

A mixture of 564 kg/hr of phenol and 58 kg/hr of acetone was passed through the catalyst layer at 70° C. under atmospheric pressure and reacted continuously. Hydrogen chloride was blown into the reaction mixture in the hydrogen chloride absorption column. The mixture thus obtained was successively charged into batchwise reactors every one hour. The second reaction was conducted with stirring for 8 hours.

The slurry obtained as the reaction product was analyzed. Compounds having three aromatic rings were almost undetected. The contents of the o,p'-isomer and Dianin's compound in bisphenol A were 1.5 wt.% and 0.2 wt.%, respectively.

COMPARATIVE EXAMPLE 1

The product obtained by the reaction in the presence of the cation exchange resin catalyst in Example 1 was analyzed. The acetone conversion ratio was 45%. The contents of the o,p'-isomer and Dianin's compound in the formed bisphenol A were 6.0 wt.% and 0.1 wt.%, respectively.

COMPARATIVE EXAMPLE 2

The same reaction as described in Comparative Example 1 was repeated except that twice the amount of the catalyst was used. The acetone conversion ratio was increased to 55%. The contents of the o,p'-isomer and Dianin's compound in bisphenol A were 6.0 wt.% and 0.1 wt.%, respectively. That is, no change was observed.

COMPARATIVE EXAMPLE 3

The same procedures described in Example 1 were repeated except the cation exchange resin catalyst was omitted. After 8 hours, the acetone conversion ratio was 99.0% and the contents of the o,p'-isomer and Dianin's compound in bisphenol A were 1.6 wt.% and 0.65 wt.%, respectively. After 10 hours, the acetone conversion ratio was 99.5%, and the contents of the o,p'-isomer and Dianin's compound in bisphenol A were 1.5 wt.% and 0.7 wt.%, respectively.

We claim:

1. A process for preparing bisphenol A by the reaction of acetone with phenol comprising:
   (a) conducting the reaction of acetone with phenol in the presence of a sulfonic acid type cation exchange resin modified with a mercapto group-containing compound to convert 20 to 60% of the acetone in the reaction; and thereafter
   (b) further reacting the resulting reaction mixture containing unreacted acetone in the presence of a hydrochloric acid catalyst.

2. The process as claimed in claim 1 wherein the mole ratio of acetone to phenol is 1:4 to 1:12.

3. The process as claimed in claim 1 wherein 5 to 35 mole % of the sulfonic acid groups in said cation exchange resin are modified with the mercapto group-containing compound.

4. The process as claimed in claim 1 wherein 12 mole % of the sulfonic acid groups in said cation exchange resin are modified with mercaptoethylamine.

5. The process as claimed in claim 1 wherein said reaction in the presence of the cation exchange resin is conducted at a temperature of 30° to 120° C.

6. The process as claimed in claim 1 wherein said reaction in the presence of the hydrochloric acid catalyst is conducted at a temperature of 30° to 85° C.

7. The process as claimed in claim 1 wherein the reaction in the presence of the cation exchange resin is conducted continuously and the reaction in the presence of the hydrochloric acid catalyst is carried out batchwise.

* * * * *